(12) United States Patent
Frost et al.

(10) Patent No.: US 10,145,770 B2
(45) Date of Patent: Dec. 4, 2018

(54) CHAIN WEAR MONITORING DEVICE

(71) Applicant: Frost Tech LLC, Grand Rapids, MI (US)

(72) Inventors: Charles C. Frost, Ada, MI (US); James A. Mitchell, Grand Rapids, MI (US)

(73) Assignee: Frost Tech LLC, Grand Rapids, MI (US)

( * ) Notice: Subject to any disclaimer, the term of this patent is extended or adjusted under 35 U.S.C. 154(b) by 429 days.

(21) Appl. No.: 14/812,328

(22) Filed: Jul. 29, 2015

(65) Prior Publication Data

US 2017/0030815 A1    Feb. 2, 2017

(51) Int. Cl.
  *G01N 3/56* (2006.01)
  *B65G 43/02* (2006.01)
  *G01M 13/02* (2006.01)

(52) U.S. Cl.
  CPC .............. *G01N 3/56* (2013.01); *B65G 43/02* (2013.01); *G01M 13/023* (2013.01); *B65G 2203/042* (2013.01); *B65G 2207/40* (2013.01)

(58) Field of Classification Search
  CPC .............. B65G 43/02; B65G 2203/042; B65G 2207/40; G01N 3/56; G01M 13/023; G01B 11/043; F16H 57/01
  See application file for complete search history.

(56) References Cited

U.S. PATENT DOCUMENTS

| | | | |
|---|---|---|---|
| 3,827,582 A * | 8/1974 | Lederer | B65G 47/28 |
| | | | 198/419.1 |
| 4,198,758 A * | 4/1980 | Eineichner | G01B 11/043 |
| | | | 198/349.95 |
| 4,274,783 A | 6/1981 | Eineichner et al. | |
| 4,566,339 A | 1/1986 | Davidson et al. | |
| 4,803,886 A | 2/1989 | May et al. | |
| 5,272,924 A | 12/1993 | Tassic et al. | |
| 5,291,131 A | 3/1994 | Suzuki et al. | |
| 5,563,392 A | 10/1996 | Brown et al. | |

(Continued)

FOREIGN PATENT DOCUMENTS

| DE | 19713560 | 12/1998 |
|---|---|---|
| EP | 1508277 | 2/2005 |

(Continued)

*Primary Examiner* — Jill Culler
*Assistant Examiner* — Leo T Hinze
(74) *Attorney, Agent, or Firm* — Mitchell Intellectual Property Law, PLLC

(57) ABSTRACT

A conveyor or drive chain wear monitor includes two sensors spaced apart from one another a predetermined distance which is less than the distance between the two selected measuring points on a chain. Two timers are provided, one of which is a chain speed timer and the other of which is the chain wear timer. The two timers are both controlled by the spaced sensors. The problem of sensor beams being broken by irrelevant beam breaking obstacles located between the successive spaced measuring points is solved by providing an ignore obstacle software routine in the wear monitor computer. The ignore obstacle software routine allows a user to program the monitor to ignore any number of irrelevant obstacles which might occur between two spaced measuring points on a chain.

11 Claims, 2 Drawing Sheets

(56) References Cited

U.S. PATENT DOCUMENTS

| | | | |
|---|---|---|---|
| 5,997,423 A * | 12/1999 | Kwon | B65G 23/44 |
| | | | 198/810.04 |
| 6,851,546 B2 | 2/2005 | Lodge | |
| 6,862,939 B2 | 3/2005 | Frost | |
| 6,993,978 B2 | 2/2006 | Frost | |
| 7,325,669 B2 | 2/2008 | Frost et al. | |
| 7,540,374 B2 | 6/2009 | Rathbun et al. | |
| 8,285,494 B2 * | 10/2012 | Vozner | G01B 11/028 |
| | | | 198/502.1 |
| 9,222,861 B2 * | 12/2015 | Urbanzyk | B65G 43/02 |
| 2003/0140709 A1 | 7/2003 | Frost | |
| 2004/0226805 A1 | 11/2004 | Lodge | |
| 2004/0237662 A1 | 12/2004 | Nassar et al. | |
| 2011/0093218 A1 | 4/2011 | Vozner | |
| 2014/0102212 A1 | 4/2014 | Urbanzyk | |

FOREIGN PATENT DOCUMENTS

| | | |
|---|---|---|
| GB | 2406844 | 4/2005 |
| JP | 61163220 | 10/1986 |
| JP | 62145105 | 6/1987 |
| JP | 63306116 | 12/1988 |
| JP | 2130402 | 5/1990 |
| JP | 2006317359 | 11/2006 |
| KR | 1020090055591 | 6/2009 |
| SU | 1063739 | 12/1983 |
| WO | 03093783 | 11/2003 |
| WO | 2008024685 | 2/2008 |

* cited by examiner

CHAIN WEAR MONITORING DEVICE

FIELD AND BACKGROUND OF THE INVENTION

The present invention relates to chain wear monitoring devices. Such devices are designed to determine the extent of wear on a chain while it is moving. Such devices are used for example to monitor wear on moving chains used in overhead conveyors. Such chains wear at the junction between the links of the chain, and often occur at the pins which are used to join adjacent links of the chain.

Often, such devices use one or more light beams or laser beams which are broken by passing measuring points on the chain. By using a first measuring point on one chain link, and a second another measuring point on a following chain link, one can use various different algorithms to determine the wear occurring between those measuring points. In U.S. Pat. No. 6,993,978, entitled Pin Detection System, pins or like projections, which project from the top of link pins in the chain, are provided as measuring points. One advantage to the use of such pins is that there are no intervening irrelevant light blocking items at which a light or laser beam might be broken. For example, some chains use guide rollers which extend across the opening between side links, and interfere with using the leading edge of successive center links as measuring points. In such a chain, the beam is broken not only by the leading edge of the center link, but by the guide roller located between successive center links.

SUMMARY OF THE INVENTION

In the chain wear monitor of the present invention, the problem of sensor beams being broken by irrelevant beam breaking obstacles located between successive measuring points is solved by providing an ignore obstacle software routine in the wear monitor computer. The ignore obstacle software routine allows a user to program the monitor to ignore any number of irrelevant obstacles which might occur between two spaced measuring points on a chain.

These and other features, objects and advantages of the invention will be more fully understood and appreciated by reference to the written specification and appended drawings.

DETAILED DESCRIPTION OF THE PREFERRED EMBODIMENT

Figure 1:
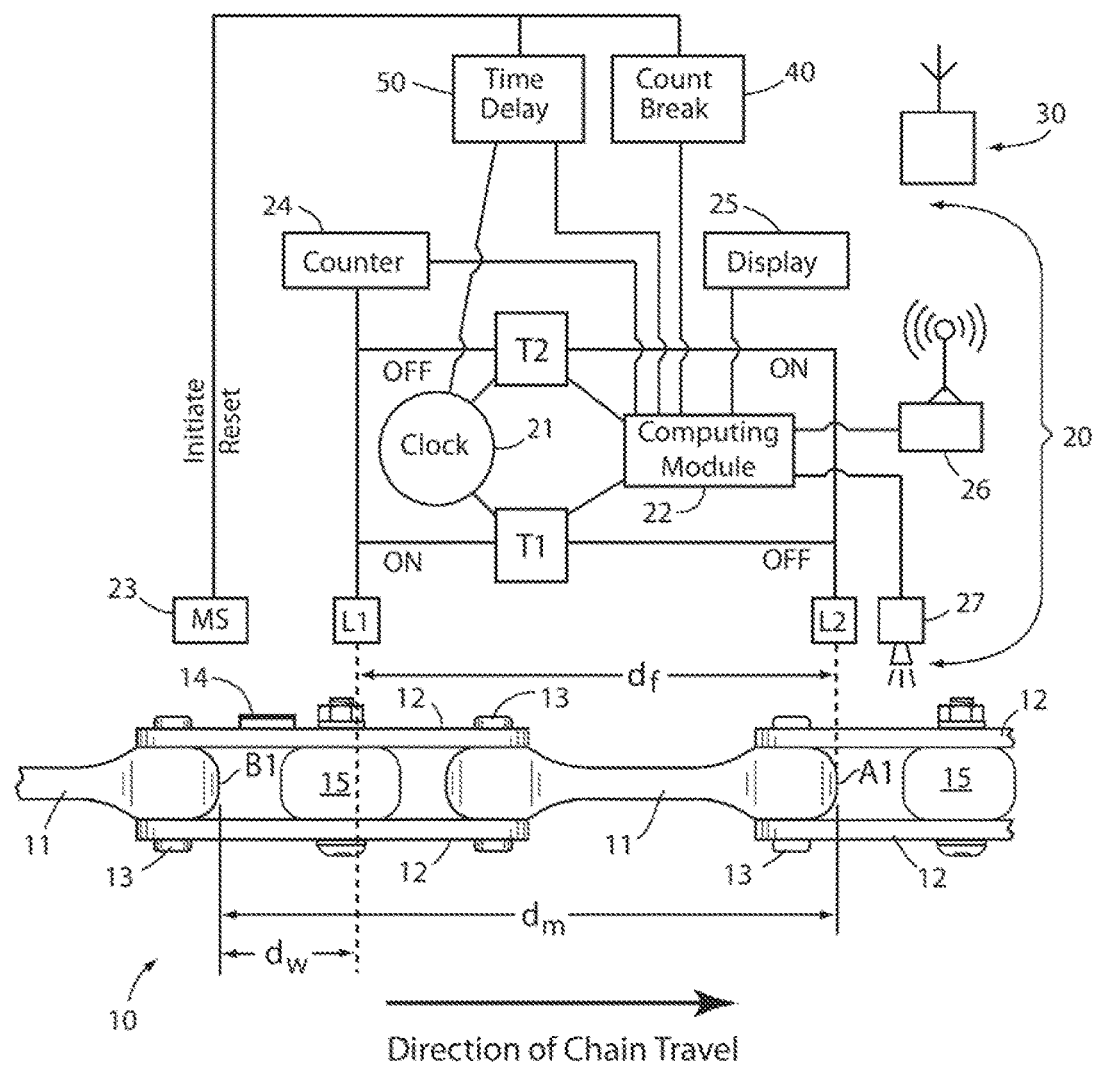
FIG. 1 shows conveyor chain as it passes a preferred embodiment wear monitor.

FIG. 1 shows a typical conveyor chain 10 as it moves passed the wear monitoring device 20 towards the right as shown in FIG. 1. Spaced center links 11 are joined to side links 12 by pins 13. In the embodiment shown, the leading edge of each center link 11 has been chosen as a measuring point. As shown, measuring point A1 would be the downstream measuring point relative to measuring point B1.

The wear monitor comprises an upstream sensor L1 and a downstream sensor L2. Sensors L1 and L2 are positioned a fixed distance $d_f$ apart. The distance $d_f$ must be a shorter distance than the "new chain" distance $d_{m-i}$ between successive measuring points on chain 10. These sensors are connected to a speed timer T1 and a wear timer T2, both of which are connected to a clock 21 and a computing module 22. The speed timer T1 and wear timer T2 include on and off triggers which are operated by signals received from the upstream and downstream sensors L1 and L2. The timers determine the passage of time through their connection to clock 21. Computing module 22 records the time which passes and uses that information to determine speed and wear.

However, the chain 10 shown in FIG. 1 utilizes guide rollers 15 mounted between the side links 12. Guide rollers 15 represent an irrelevant beam breaking point between the desired measuring points A1 and B1. The preferred embodiments of the wear monitor of the present invention afford two different ways to implement the ignore obstacle software routine of the invention. The first is a "count break" software routine 40, which the user can program to directly ignore any desired number of beam breaks occurring between the desired measuring points A1, B1 on the chain 10. When the sensor L1 or L2 senses the desired measuring point by having its beam broken, the count break routine 40 causes the wear monitor to ignore the next one or more beam breaks which occur, based on the number which the user has entered into the monitor.

The second is a "time delay" software routine 50 which creates a delay between the sensing of the desired beam breaking point by the beam of sensors L1 and L2, and the time at which the sensor will again sense an obstacle. At the initial sensing, software routine 50 deactivates the sensor L1 or L2. It then delays reactivation of the sensor for the determined period of the time delay. This time delay is determined by the software routine 50 based on the speed of the chain and the distance the between desired measuring points. The delay in reactivation of the sensor is sufficient to prevent the sensors from recognizing intervening irrelevant beam breaking obstacles such as guide roller 15, but short enough to reactivate the sensor before the desired measuring point arrives at the sensor. In the wear monitor embodiment included herein, the speed is determined substantially instantaneously as the chain passes sensors L1 and L2. By programming the known distance between desired wear points into the time delay routine, the software will calculate the necessary time delay and implement it as a function of the indicated time passing on clock 21, and the time of last activation of sensor L1 or L2, respectively.

The "deactivation of the sensor" may be accomplished by actually turning the sensor off. However, it is preferably accomplished by simply ignoring any breaking of the sensor beam during the delay time.

With either the count break routine 40 or the time delay routine 50, it is believed that the system can begin counting with any of the beam interrupting obstacles being used, so long as the appropriate number of obstacles is ignored by the system. However, one may prefer to tell the system when to "start." This is accomplished by using a separate sensor to sense a start location on the chain, which is just ahead of a desired measuring point on the chain. In the preferred embodiment, this is accomplished using a magnetic sensor 23 as the separate sensor, and a magnet 14 as the object to be sensed. The magnet 14 is placed on chain 10 at a point just ahead of a desired measuring point on the chain. When the magnet sensor 23 senses magnet 14, it informs count break routine 40 or time delay routine 50 to "start." The position of the magnet sensor 23 and beam sensor L1 is arranged such that the next breaking of the beam from sensor L1 will be the passing of the next desired measuring point, which is B1 as shown in FIG. 1. When sensor L1 senses measuring point B1, both sensor L1 and sensor L2 are "deactivated" by time delay routine 50. Alternatively, count break routine 40 counts the next obstacle which sensor L1 and L2 "see" by having their beams broken, which as shown in FIG. 1 will be guide roller 15. Since that will be the only irrelevant break as shown in FIG. 1, it is the only sensor beam break which count break routine 40 will ignore, and the next beam break after that will be counted.

The irrelevant beam break obstacles do not have to be interruptions such as guide roller 15. A user with a chain having no such interruptions might simply wish to use as measuring points A1 and B1 the leading edges of center links which are several links apart, rather than being adjacent as shown in FIG. 1. Thus, the leading edges of several intervening center links will break the light or laser beam between desired measuring points A1 and B1. Using the preferred embodiment wear monitors of the present invention, these intervening beam breaking obstacles will be ignored by the wear monitor.

With the wear monitor programmed by the user to ignore irrelevant intervening break obstacles, the wear monitor will then operate in the manner set forth hereinafter, as though there were no such intervening obstacles in the chain. Thus, for example, no intervening obstacles are even illustrated in the chain 10 shown in FIG. 2.

In operation, speed timer T1 is turned on every time upstream sensor L1 senses the passage of a measuring point, e.g. A1, B1, etc. At the same time, upstream sensor L1 turns off the wear timer T2. Thus when any measuring point on the chain passes sensor L1, the speed timer T1 is turned on and the wear timer T2 is turned off.

The downstream sensor L2 turns the speed timer T1 off every time it senses the passage of a measuring point, A1, B1, etc., ignoring any intervening irrelevant beam breaking points. On the other hand, downstream sensor L2 turns wear timer T2 on every time a measuring point passes it. Thus, when upstream sensor L1 senses the passage of a measuring point, speed timer T1 is turned on, and is not turned off again until that same measuring point passes downstream sensor L2. Knowing the fixed distance $d_f$ between upstream and downstream sensors L1 and L2, and the speed time $t_1$ which timer T1 was on, computing module 22 can calculate the speed at which chain 10 is moving:

$$\text{Speed } S = \frac{\text{fixed distance } d_f}{\text{speed time } t_1 \text{ as determined by } T1}$$

Thus as shown in FIG. 1, speed of chain 10 is being determined based on the time $t_1$ it took measuring point A1 to get from sensor L1 to sensor L2.

As measuring point A1 passes sensor L2, wear timer T2 is turned on, at the same time speed timer T1 is turned off. Timer T2 will not turn off until the successive measuring point B1 passes sensor L1. Computing module 22 can determine the degree of wear on the chain as a function of the speed S of the chain and the wear time $t_2$ which timer T2 is on, as compared to the baseline value for the same function when the chain is new. This can be accomplished in at least two different ways.

One formula compares the distance $d_m$ as measured currently to the initial distance $d_{m-i}$ between the two measuring points, referred to as the "baseline value." Using the speed S of the chain and the wear time $t_2$ as determined by wear timer T2, computing module 22 can determine the distance $d_m$ between the two successive measuring points A1 and B1 as follows:

$$d_m = (S \cdot t_2) + d_f$$

Since computer 22 has either determined or been programmed to know what the initial distance $d_{m-i}$ (the baseline value in this equation) was when chain 10 was new, computer 22 can determine the degree of wear by subtracting $d_{m-i}$ from $d_m$:

$$\text{Wear } W = d_m - d_{m-i}$$

Computing module 22 is programmed such that an operator can enter the distance between successive measuring points A1, B1, etc. when the chain is new ($d_{m-i}$). The initial distance $d_{m-i}$ input into computing module 22 can be based on operator input of the "as manufactured" distance between said wear points. Preferably, however, the input indicating the initial distance between each successive pair of measuring points is determined and recorded in computing module 22 as a result of the measurements taken by wear monitor 20 during the first pass of chain 10 passed wear monitor 20. The operator thus has saved in computer 22 a precise measurement of the initial distance $d_{m-i}$ between each adjacent pair of measuring points on chain 10. This eliminates error caused by manufacturing variability, and makes the wear measurement ultimately taken more accurate. Indeed, it gives an accurate measurement of $d_{m-i}$ for each link set in the chain.

Figure 2:
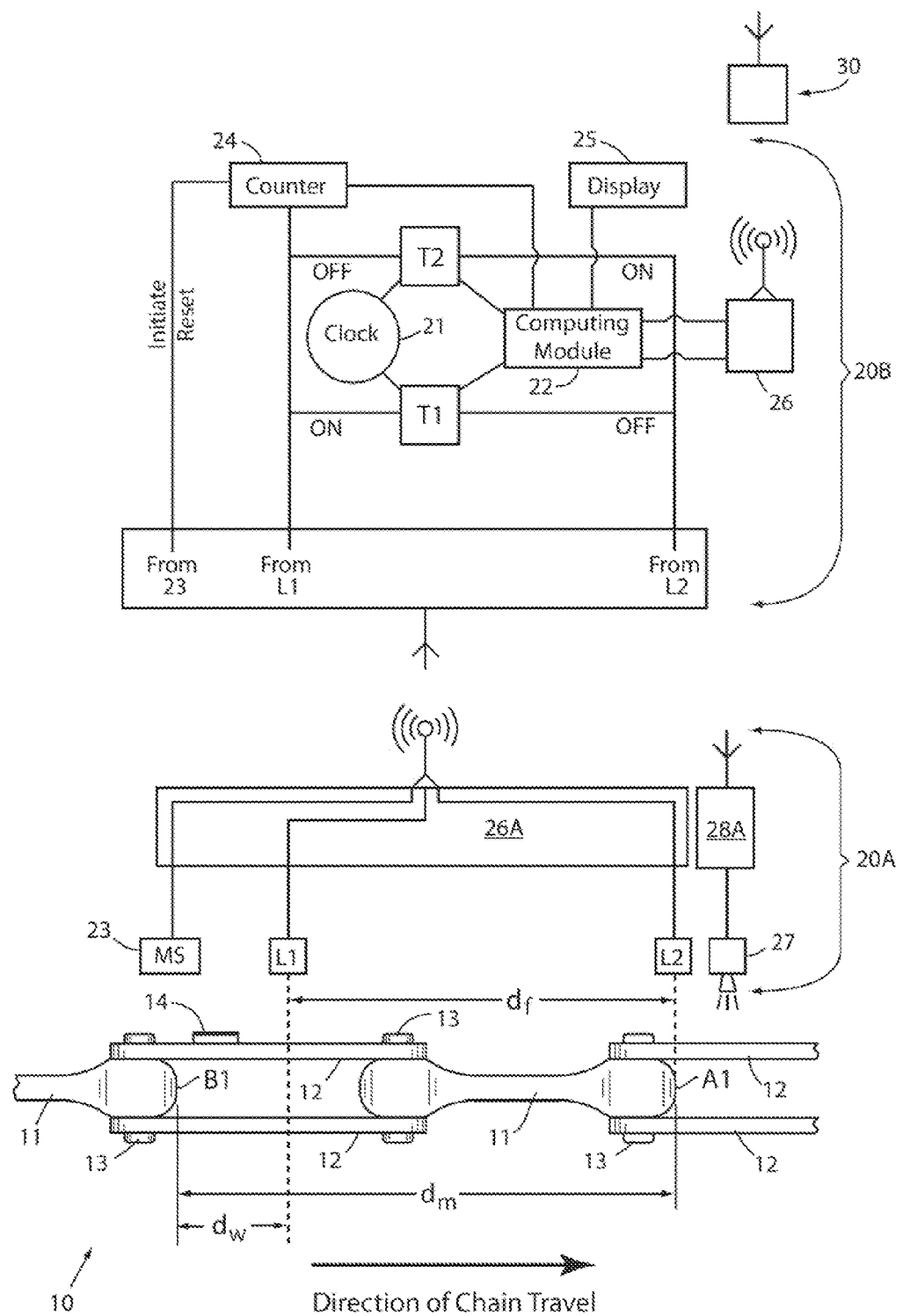
FIG. 2 discloses an alternative embodiment in which wear monitor 20 is divided into a sensor unit 20A and a computing module unit 20B.

In a second formula, the computing module can be programmed to determine only the distance $d_w$ traveled by the chain during the time $t_2$ during which wear timer T2 is on. The distance $d_w$ is referred to for convenience as the "wear distance," since it is used to determine chain wear. As seen in FIGS. 1 and 2, the wear distance is the distance $d_m$ between adjacent measuring points on chain 10, less the distance $d_f$ between upstream and downstream sensors L1 and L2:

$$d_w = d_m - d_f$$

Said another way, wear distance is the distance traveled by the chain between the time a measuring point A1 on chain 10 turns timer T2 on, until the subsequent measuring point B1 turns timer T2 off. Wear can be determined by comparing the initial distance $d_{w-i}$ (the baseline value in this equation) for a new chain to the $d_w$ measured on any subsequent pass of the chain past wear monitor 20, as follows:

$$d_w = (S \cdot t_2) \; d_{w-i} = (S \cdot t_2) \text{ for a new chain.}$$

$$\text{Wear } W = d_w - d_{w-i}$$

As above, the initial wear distance $d_{w-i}$ (the baseline value), can be programmed into computing module 22 using "as manufactured" data, or can be determined on the first pass of a new chain past wear monitor 20.

The accuracy of the speed and wear determinations made by wear monitor 20 is in part a function of the distance between the upstream sensor L1 and the downstream sensor L2. As noted above, the sensors need to be spaced a distance which is less than the distance between adjacent measuring points A1 and B1 on chain 10. Within those confines, the accuracy of the speed determination is enhanced by spacing the sensors as far apart as possible, and the accuracy of the wear determination is enhanced by spacing the sensors as close together as possible. As a starting point, the distance between sensors L1 and L2 must be such that reasonably accurate speed and wear measurements can be obtained. Preferably, one of the sensors is moveably mounted relative to the other such that the sensors can be spaced at a distance equal to about half to three quarters of the space between adjacent measuring points on chain 10, most preferably about half. Preferably, each measuring point is associated with a single link set, such that the spacing $d_f$ is equal to about half to three quarters of the nominal pitch of the chain 10 being monitored, most preferably, about half. In the alternative, fixedly mounted sensors can be spaced at a distance equal to about half to three quarters of the nominal pitch of the smallest pitch chain 10 to be monitored, most preferably, about three quarters.

In the preferred embodiment, chain 10 is provided with a location marker 14, positioned between a pair of adjacent measuring points. Wear monitor 20 includes a location marker sensor 23 which initiates or resets a counter 24. Counter 24 is also connected to upstream sensor L1 and to computing module 22. Downstream sensor L2 could also be used, but upstream sensor L1 is preferred. When wear monitor 20 is first turned on, counter 24 is idle until such time as marker sensor 23 senses location marker 14. Location marker 14 is not sensed by either upstream or downstream sensors L1 and L2. It is only sensed by marker sensor 23. When location marker is sensed by marker sensor 23, counter 24 is initiated, or if it has already been running, is reset to 0. When thereafter upstream sensor L1 senses a measurement point, counter 24 counts the sensing. Preferably, marker sensor 23 is located within one link set of upstream sensor L1, so that computing module 22 would be recording the first link set after location marker 14 as link set number 1. Subsequent link sets would be number 2, 3, 4, seriatim, until marker 14 passes marker sensor 23 again, resulting in a re-set of counter 24. The computing module will keep track of wear data for each numbered link set, for each successive pass by wear monitor 20. Of course, the display of the recorded information is preferably adjustable as a function of wear rate, such that one could show the wear data at spaced passage intervals, e.g. every ten passes or every 25 passes, etc.

In one embodiment, measuring points are selected so that there is one measuring point for each "link set." In some types of chains, a link set may be a single link. In the conveyor chain 10 shown in the preferred embodiment, a link set comprises one center link 11 and a pair of side links 12 connected by pin 13. Computing module 22 correlates link set count with the degree of wear shown for that link set on that pass. This information is recorded by the computing module 22. In this way, an operator can determine the wear at each link set on any given pass by the wear monitor. However as noted above, the measuring points could be selected to encompass several link sets, and programmed to ignore the passage of beam breaking points occasioned by irrelevant intervening link sets.

Each time marker sensor 23 resets counter 24, it also triggers computing module 22 to start recording a subsequent series of wear monitor measurements for each subsequent pass of the link sets passing wear monitor 20. In this way, computing module 22 retains a record of measurements for each link set for each complete revolution of chain 10 past wear monitor 20. Computing module 22 is also preferably hard wired or programmed to generate a graph showing the rate of increase of wear for each numbered link set over time.

Preferably, marker sensor 23 would be a different type of sensor from upstream and downstream measuring sensors L1 and L2. This would avoid any possibility of either of the measuring sensors L1 or L2 mistakenly sensing location marker 14 as a passing measuring point A1, B1, etc. In a preferred embodiment, marker 14 is a magnet, and marker sensor location marker sensor 23 is a magnetic sensor. On the other hand, measuring sensors L1 and L2 are preferably laser sensors, which sense the passing measuring points by having its laser beam broken between the laser sensor and a beam receiver.

In one embodiment, the measuring points A1, B1, etc. constitute the leading edge of each center link 11. Other measuring points could be selected, but preferably the measuring points are selected such that each measuring point is unique to a single link set. The measuring points could comprise projections extending upwardly (or downwardly) from the top or bottom of the link pins 13. In keeping with the concept of each measuring point representing a single link set, such projections would be placed on every other link pin 13 of chain 10, since a link set comprises two links, namely a center link 11 and a pair of side links 12. Such projections are disclosed in U.S. Pat. No. 6,862,939.

Wear monitor 20 preferably includes an internal display 25 connected to computing module 22. Computing module 22 can be programmed to display different types of information. Thus, computing module 22 could display the instantaneous speed and wear measurements being taken for each link set. It could display a running average for speed and wear. It could display a graph showing the rate of increase in wear of any given link set. Computing module 22 could be programmed to display and/or sound an alarm when chain wear at any point in chain 10 becomes excessive. Similarly, computing module 22 could be connected to a painter 27 which would paint a passing link set which had shown too much wear. On the other hand, by actually numbering the link sets in chain 10, beginning with number 1 for the link set immediately following location marker 14, one could readily find the over worn link set, since it would also be identified by computing module 22 in accordance with its link set number.

Preferably, monitor 20 includes not only an internal display, but also includes a transmitter 26 which will transmit display information to a printer or to an external computer or computer display 30. In this way, an operator could locate himself anyplace relative to chain 10, or move about while observing the operation of chain 10, and still view pertinent information on his computer/display 30. Transmitter 26 can also transmit instructions to a printer, to print out the results of the computing module's analysis of the chain wear.

FIG. 2 discloses an alternative embodiment in which wear monitor 20 is divided into two separate units: a sensor unit 20A and a controller unit 20B. Sensor unit 20A preferably comprises marker sensor 23, and measuring sensors L1 and L2, all coupled to a transmitter 26A, and a painter 27 connected to a receiver 28A. All of the remaining functions shown in FIG. 1 are preferably contained in controller 20B, which would include a receiver 28 for receiving the transmission from transmitter 26A, and a transmitter 26 for transmitting a "paint" signal to receiver 28A. That signal would then activate painter 27 to paint the defective link. The transmitter 26A would assign a unique frequency or frequency variation to each sensor, so the controller 20B would recognize which sensor it is receiving a signal from. Similarly, transmitter 26A uses a unique frequency or frequency variation for the paint signal.

In this embodiment, controller 20B can be either a dedicated hard wired unit, or it can be a personal computer device of any kind, programmed with a software application containing the timer circuits T1 and T2, the clock function 21, the computing module 22, the counter 24 and the display controller 25 which would simply operate the display on the personal computer device.

Transmitter 26A would also be used to transmit computer information to a printer or to another person's personal computer device 30. The term "personal computer device" as used herein refers to any type of computer including a receiver and preferably a transmitter for receiving and transmitting information. It could be a laptop computer, a desktop computer, a handheld computer telephonic device, etc. In all cases where a transmitter and a receiver are called for in a single unit, a transmitter/receiver unit could be used to accomplish both functions.

Of course, it is understood that the above are merely preferred embodiments of the invention and that various changes and alterations can be made without departing from the spirit and broader aspects of the invention, as set forth in the appended claims, as interpreted in accordance with the doctrine of equivalents.

The invention claimed is:

1. A chain wear monitor comprising:
at least one measuring point sensor projecting a sensor beam for sensing predetermined spaced measuring points on a chain;
a computing module which determines the degree of wear in the chain between two spaced measuring points;
said computing module including an ignore obstacle software routine, which can be programmed by the user to ignore any number of beam breaking obstacles which might occur between said two spaced measuring points on the chain;
said ignore obstacle software routine of said computing module being a "count break" software routine, which the user can program to ignore any desired number of beam breaks occurring between the desired measuring points on the chain;
a start sensor which senses a start location on said chain which, in the direction of travel of said chain, is just ahead of a desired measuring point on said chain;
said start sensor starting said count break software routine when it senses a start location on said chain; and
after said measuring point sensor senses the following measuring point, said count break software routine deactivating said sensor, by causing said computing module to disregard the selected number of beam breaks occurring thereafter.

2. The chain wear monitor of claim 1 which:
there are two of said measuring point sensors for sensing predetermined spaced measuring points on a chain, said two measuring point sensors being spaced apart from one another a predetermined distance which is less than the distance between adjacent ones of said spaced measuring points on said chain;
said count break routine deactivating both of said measuring point sensors simultaneously and reactivating them simultaneously;
one of said measuring point sensors being the upstream measuring point sensor, as determined by the direction of travel of the chain, and the other of said measuring point sensors being the downstream measuring point sensor;
two timers, one of which is a chain speed timer and the other of which is the chain wear timer, both said timers being controlled by said spaced measuring point sensors;
said upstream measuring point sensor acting to turn said chain speed timer on and said wear timer off when sensing the passage of one of said measuring points on said chain;
said downstream measuring point sensor acting to turn said speed timer off and said wear timer on when it senses the passage of one of said measuring points on said chain;
said computing module determining the speed at which said chain is moving as a function of the length of time, as determined by said speed timer, which it takes a measuring point on the chain to pass from said upstream measuring point sensor to said downstream measuring point sensor;
said computing module determining the degree of wear on said chain as a function of the speed of the chain and the wear time which said wear timer is on, as compared to the baseline value for the same function when the chain is new.

3. The chain wear monitor of claim 2 which:
said start location is a magnet located on said chain, and said start sensor is a magnetic sensor.

4. The chain wear monitor of claim 1 which:
there are two of said measuring point sensors for sensing predetermined spaced measuring points on a chain, said two measuring point sensors being spaced apart from one another a predetermined distance which is less than the distance between adjacent ones of said spaced measuring points on said chain;
one of said measuring point sensors being the upstream measuring point sensor, as determined by the direction of travel of the chain, and the other of said measuring point sensors being the downstream measuring point sensor;
two timers, one of which is a chain speed timer and the other of which is the chain wear timer, both said timers being controlled by said spaced measuring point sensors;
said upstream measuring point sensor acting to turn said chain speed timer on and said wear timer off when sensing the passage of one of said measuring points on said chain;
said downstream measuring point sensor acting to turn said speed timer off and said wear timer on when it senses the passage of one of said measuring points on said chain;
said ignore obstacle software routine causing said computing module to ignore beam breaking obstacles which occur between said two spaced measuring points on the chain;
said computing module determining the speed at which said chain is moving as a function of the length of time, as determined by said speed timer, it takes a measuring point on the chain to pass from said upstream measuring point sensor to said downstream measuring point sensor;
said computing module determining the degree of wear on said chain as a function of the speed of the chain and the wear time which said wear timer is on, as compared to the baseline value for the same function when the chain is new.

5. The chain wear monitor of claim 4 which:
said ignore obstacle software routine of said computing module is a "count break" software routine, which the user can program to ignore any desired number of beam breaks occurring between the desired measuring points on the chain.

6. The chain wear monitor of claim 4 which:

said ignore obstacle software routine of said computing module is a "time delay" software routine which creates a delay between the sensing of a desired measuring point by the breaking of the beam of said upstream measuring point sensor, and the time at which said downstream measuring point sensor will again sense an obstacle, which time delay is long enough to avoid detecting irrelevant obstacles, but short enough to reactivate said downstream measuring point sensor before the desired measuring point arrives at said sensor.

7. A chain wear monitor comprising:

at least one measuring point sensor projecting a sensor beam for sensing predetermined spaced measuring points on a chain;

a computing module which determines the degree of wear in the chain between two spaced measuring points;

said computing module including an ignore obstacle software routine, which can be programmed by the user to ignore any number of beam breaking obstacles which might occur between said two spaced measuring points on the chain;

said ignore obstacle software routine of said computing module is a "time delay" software routine which creates a delay between the sensing of a desired measuring point by the breaking of the beam of said measuring point sensor, and the time at which said measuring point sensor will again sense an obstacle, which time delay is long enough to avoid detecting irrelevant obstacles, but short enough to reactivate said sensor before the desired measuring point arrives at said sensor.

8. The chain wear monitor of claim 7 which:

said time delay is determined by said software routine based on the speed of said chain and the distance the between said two spaced measuring points.

9. The chain wear monitor of claim 8 which said wear monitor includes:

a start sensor which senses a start location on said chain which, in the direction of travel of said chain, is just ahead of a desired measuring point on said chain;

said start sensor starting said time delay software routine when it senses a start location on said chain; and after said measuring point sensor senses the measuring point which follows said start location, said time delay software routine deactivating said sensor, by causing said computing module to disregard the beam breaks occurring thereafter for the period of said time delay.

10. The chain wear monitor of claim 9 which:

there are two of said measuring point sensors for sensing predetermined spaced measuring points on a chain, said two measuring point sensors being spaced apart from one another a predetermined distance which is less than the distance between adjacent ones of said spaced measuring points on said chain;

said time delay software routine deactivating both of said measuring point sensors simultaneously and reactivating them simultaneously;

one of said measuring point sensors being the upstream measuring point sensor, as determined by the direction of travel of the chain, and the other of said measuring point sensors being the downstream measuring point sensor;

two timers, one of which is a chain speed timer and the other of which is the chain wear timer, both said timers being controlled by said spaced measuring point sensors;

said upstream measuring point sensor acting to turn said chain speed timer on and said wear timer off when sensing the passage of one of said measuring points on said chain;

said downstream measuring point sensor acting to turn said speed timer off and said wear timer on when it senses the passage of one of said measuring points on said chain;

said computing module determining the speed at which said chain is moving as a function of the length of time, as determined by said speed timer, it takes a measuring point on the chain to pass from said upstream measuring point sensor to said downstream measuring point sensor;

said computing module determining the degree of wear on said chain as a function of the speed of the chain and the wear time which said wear timer is on, as compared to the baseline value for the same function when the chain is new.

11. The chain wear monitor of claim 10 which:

said start location is a magnet located on said chain, and said start sensor is a magnetic sensor.

* * * * *